(12) United States Patent
Schwiegerling et al.

(10) Patent No.: US 9,681,800 B2
(45) Date of Patent: Jun. 20, 2017

(54) HOLOGRAPHIC ADAPTIVE SEE-THROUGH PHOROPTER

(71) Applicant: The Arizona Board of Regents on Behalf of the University of Arizona, Tucson, AZ (US)

(72) Inventors: James T. Schwiegerling, Tucson, AZ (US); Nasser N. Peyghambarian, Tucson, AZ (US); Gholam A. Peyman, Sun City, AZ (US); Nickolaos Savidis, Tucson, AZ (US)

(73) Assignee: The Arizona Board of Regents on Behalf of The University of Arizona, Tucson, AZ (US)

( * ) Notice: Subject to any disclaimer, the term of this patent is extended or adjusted under 35 U.S.C. 154(b) by 649 days.

(21) Appl. No.: 13/791,665

(22) Filed: Mar. 8, 2013

(65) Prior Publication Data

US 2013/0182224 A1    Jul. 18, 2013

Related U.S. Application Data

(63) Continuation of application No. PCT/US2012/071255, filed on Dec. 21, 2012, and a
(Continued)

(51) Int. Cl.
*A61B 3/028* (2006.01)
*A61F 2/16* (2006.01)
(Continued)

(52) U.S. Cl.
CPC .......... *A61B 3/0285* (2013.01); *A61B 3/1015* (2013.01); *A61F 2/1635* (2013.01); *G02B 3/14* (2013.01); *G02B 5/32* (2013.01)

(58) Field of Classification Search
CPC ...... A61B 3/1015; A61B 3/0285; G02B 5/32; G02B 3/14; A61F 2/1635
(Continued)

(56) References Cited

U.S. PATENT DOCUMENTS 4,373,218 A    2/1983    Schachar
4,563,565 A    1/1986    Kampfer et al.
(Continued)

FOREIGN PATENT DOCUMENTS

WO    WO2013/096775    6/2013

OTHER PUBLICATIONS

Marks et al., Adjustable adaptive compact fluidic phoropter with no mechanical translation of lenses, Optics Letters, Mar. 1, 2010, vol. 35, No. 5, pp. 739-741.*
(Continued)

*Primary Examiner* — David Porta
*Assistant Examiner* — Gisselle Gutierrez
(74) *Attorney, Agent, or Firm* — Barry L. Davison; Davis Wright Tremaine LLP (57) ABSTRACT

A phoropter having a line of sight for a viewer to see through comprises a lens system in the line of sight, wherein a shape or focal length of at least one lens in the lens system is controllable by means of an electrical signal, electrical field or current. Wavefront sensors of the phoropter detect local tilts of light wavefronts emerging from the eye and generate output signals that are used for controlling the shape or focal length of the at least one lens. Holographic or diffractive elements are used to collect light scattered from an eye of the viewer and image the scattered light to the wavefront sensors. Preferably one or more of the holographic or diffractive elements are away from the line of sight of the viewer. To use the phoropter, light is passed to the lens system, and light scattered by the eye is collected by the
(Continued)

holographic or diffractive elements and imaged onto the wavefront sensors.

14 Claims, 9 Drawing Sheets

Related U.S. Application Data continuation-in-part of application No. 13/165,231, filed on Jun. 21, 2011, now Pat. No. 8,409,278, which is a continuation-in-part of application No. 11/426,224, filed on Jun. 23, 2006, now Pat. No. 7,993,399, which is a continuation-in-part of application No. 11/259,781, filed on Oct. 27, 2005, now abandoned.

(60) Provisional application No. 61/630,889, filed on Dec. 21, 2011.

(51) Int. Cl.
*G02B 3/14* (2006.01)
*G02B 5/32* (2006.01)
*A61B 3/10* (2006.01)

(58) Field of Classification Search
USPC .......... 351/234, 246, 205, 159.44, 223, 233; 250/341.8
See application file for complete search history.

(56) References Cited

U.S. PATENT DOCUMENTS

| | | | |
|---|---|---|---|
| 4,573,998 A | 3/1986 | Mazzocco | |
| 4,575,373 A | 3/1986 | Johnson | |
| 4,676,790 A | 6/1987 | Kern | |
| 4,685,921 A | 8/1987 | Peyman | |
| 4,718,418 A | 1/1988 | L'Esperance, Jr. | |
| 4,731,078 A | 3/1988 | Stoy et al. | |
| 4,787,903 A | 11/1988 | Grendahl | |
| 4,816,031 A | 3/1989 | Pfoff | |
| 4,840,175 A | 6/1989 | Peyman | |
| 4,892,543 A | 1/1990 | Turley | |
| 4,932,966 A | 6/1990 | Christie | |
| 4,976,709 A | 12/1990 | Sand | |
| 4,994,058 A | 2/1991 | Raven et al. | |
| 5,098,444 A | 3/1992 | Feaster | |
| 5,120,121 A | 6/1992 | Rawlings et al. | |
| 5,182,585 A | 1/1993 | Stoner | |
| 5,196,027 A | 3/1993 | Thompson | |
| 5,201,762 A | 4/1993 | Hauber | |
| 5,336,261 A | 8/1994 | Barrett et al. | |
| 5,443,506 A | 8/1995 | Garabet | |
| 5,476,515 A | 12/1995 | Kelman et al. | |
| 5,607,472 A | 3/1997 | Thompson | |
| 5,647,865 A | 7/1997 | Swinger | |
| 5,722,971 A | 3/1998 | Peyman | |
| 5,824,086 A | 10/1998 | Silvestrini | |
| 5,876,442 A | 3/1999 | Lipshitz et al. | |
| 5,919,185 A | 7/1999 | Peyman | |
| 5,928,283 A | 7/1999 | Gross | |
| 6,066,171 A | 5/2000 | Lipshitz | |
| 6,102,946 A | 8/2000 | Nigam | |
| 6,142,630 A | 11/2000 | Koester | |
| 6,186,628 B1 | 2/2001 | Van de Velde | |
| 6,197,019 B1 | 3/2001 | Peyman | |
| 6,357,875 B1 | 3/2002 | Herrick | |
| 6,358,280 B1 | 3/2002 | Herrick | |
| 6,361,560 B1 | 3/2002 | Nigam | |
| 6,413,276 B1 | 7/2002 | Werblin | |
| 6,450,642 B1 | 9/2002 | Jethmalani | |
| 6,595,642 B2 | 7/2003 | Wirth | |
| 6,596,026 B1 | 7/2003 | Gross | |
| 6,673,067 B1 | 1/2004 | Peyman | |
| 6,702,807 B2 | 3/2004 | Peyman | |
| 6,749,632 B2 | 6/2004 | Sandstedt | |
| 6,806,988 B2 | 10/2004 | Onuki | |
| 6,813,097 B2 | 11/2004 | Jethmalani | |
| 6,824,266 B2 | 11/2004 | Jethmalani | |
| 6,851,804 B2 | 2/2005 | Jethmalani | |
| 6,935,743 B2 | 8/2005 | Shadduck | |
| 6,947,782 B2 | 9/2005 | Schulman | |
| RE38,839 E * | 10/2005 | Magnante ............ A61B 3/1015 219/121.75 |
| 7,036,934 B1 * | 5/2006 | Youssefi .................. G01J 9/00 351/205 |
| 7,041,133 B1 | 5/2006 | Azar | |
| 7,182,780 B2 | 2/2007 | Terwee et al. | |
| 7,413,306 B2 | 8/2008 | Campbell | |
| 7,993,399 B2 | 8/2011 | Peyman | |
| 8,409,278 B2 | 4/2013 | Peyman | |
| 9,016,860 B2 | 4/2015 | Peyman | |
| 9,191,568 B2 | 11/2015 | Peyman | |
| 2002/0016629 A1 | 2/2002 | Sandstedt et al. | |
| 2002/0042004 A1 | 4/2002 | Sandstedt | |
| 2002/0118464 A1 | 8/2002 | Nishioka | |
| 2002/0167735 A1 | 11/2002 | Jethmalani | |
| 2002/0169505 A1 | 11/2002 | Jethmalani | |
| 2002/0197584 A1 | 12/2002 | Kendir | |
| 2003/0018383 A1 | 1/2003 | Azar | |
| 2003/0048411 A1 | 3/2003 | Jethmalani | |
| 2003/0060878 A1 | 3/2003 | Shadduck | |
| 2003/0090013 A1 | 5/2003 | Jethmalani | |
| 2003/0090624 A1 | 5/2003 | Jethmalani | |
| 2003/0093150 A1 | 5/2003 | Jethmalani | |
| 2003/0128336 A1 | 7/2003 | Jethmalani | |
| 2003/0147046 A1 | 8/2003 | Shadduck | |
| 2003/0151825 A1 | 8/2003 | Bielawski | |
| 2003/0151831 A1 | 8/2003 | Sandstedt | |
| 2003/0176521 A1 | 9/2003 | Jethmalani | |
| 2004/0082993 A1 | 4/2004 | Woods | |
| 2005/0099597 A1 | 5/2005 | Sandstedt | |
| 2005/0140922 A1 | 6/2005 | Bekerman | |
| 2006/0106426 A1 * | 5/2006 | Campbell ............ G02B 26/004 607/3 |
| 2007/0046948 A1 | 3/2007 | Podoleanu | |
| 2007/0156021 A1 | 7/2007 | Morse | |
| 2007/0171366 A1 | 7/2007 | Su et al. | |
| 2007/0188882 A1 | 8/2007 | Cernasov | |
| 2007/0211207 A1 | 9/2007 | Lo | |
| 2008/0030682 A1 | 2/2008 | Teige | |
| 2008/0158508 A1 | 7/2008 | Kawashima | |
| 2008/0192201 A1 * | 8/2008 | Wengler ................. A61B 3/028 351/205 |
| 2009/0021696 A1 | 1/2009 | Chang et al. | |
| 2009/0185132 A1 * | 7/2009 | Raymond ............ A61B 3/1015 351/205 |
| 2010/0118414 A1 | 5/2010 | Bolis | |
| 2010/0149490 A1 * | 6/2010 | Olivier ................. G02B 17/004 351/206 |
| 2010/0157438 A1 | 6/2010 | Griffith | |
| 2010/0208357 A1 * | 8/2010 | Batchko .................... G02B 3/14 359/666 |
| 2010/0211167 A1 | 8/2010 | Glazier | |
| 2011/0040376 A1 | 2/2011 | Christie | |
| 2012/0038883 A1 | 2/2012 | Peyman et al. | |
| 2012/0069303 A1 * | 3/2012 | Seesselberg ......... A61B 3/1015 351/221 |
| 2013/0176537 A1 * | 7/2013 | Thompson ............. A61B 3/032 351/239 |
| 2013/0182224 A1 * | 7/2013 | Schwiegerling ..... A61B 3/1015 351/234 |

OTHER PUBLICATIONS

Marks et al., Astigmatism and defocus wavefront correction via Zernike modes produced with fluidic lenses, Applied Optics, Jul. 1, 2009, 48(19): 3580-3587.*

Savidis, Application and System Design of Elastomer Based Optofluidic Lenses, University of Arizona College of Optical Sciences, Oct. 11, 2012.*

(56) References Cited

OTHER PUBLICATIONS

Notification of Transmittal of the International Search Report and the Written Opinion of the International Searching Authority, or the Declaration for Int'l Application No. PCT/US2012/071255 mailed Apr. 3, 2013, 11 pages.

List of Claims as filed for Int'l Application No. PCT/US2012/071255 filed Dec. 21, 2012, 4 pages.

Sletten, M.D. et al., Experimental Science, "An In Vivo Model of Femtosecond Laster Intrastromal Refractive Surgery," Ophthalmic Surgery and Lasers, Nov.-Dec. 1999, vol. 30, No. 9, pp. 742-749.

Cao, Y., et al., "Comparative Study of the Use of Poly(glycolic acid), Calcium Alginate and Pluronics in the Engineering of Autologous Porcine Cartilage," Journal of Biomaterials Science, Polymer Edition 9(5):475-487, 1998.

"Did You Know?," Optics and Photonics News 16(5):8, May 2005.

Griffith, M., et al., "Functional Human Corneal Equivalents Constructed From Cell Lines," Science 286(5447):2169-2172, Dec. 10, 1999.

Ijima, H., et al., "Formation of Spherical Multicellular Aggregate (Spheroid) of Animal Cells in the Pores of Polyurethane Form as a Cell Culture Substratum and its Application to a Hybrid Artificial Liver," Jounal of Biomaterials Science, Polymer Edition 9(7):765-778, 1998.

Sheriff, L., "Liquid Lenses for Camera Phones," The Register, <http://www.theregister.co.uk/2004/12/01/vairoptics_liquid_lens/> [retrieved Jun. 1, 2016], Dec. 1, 2004, 4 pages.

Varioptic—Liquid Lens Solutions, a Business Unit of Parrot, <http://www.varioptic.com> [retrieved Jul. 6, 2016], Dec. 2005, 3 pages.

Yamauchi, K., et al., "Cultivation of Fibroblast Cells on Keratin-Coated Substrata," Journal of Biomaterials Science, Polymer Edition 9(3):259-270, 1998.

Zhang, D.-Y., et al., "Integrated Fluidic Adaptive Zoom Lens," Optics Letters 29(24):2855-2857, Dec. 15, 2004.

International Search Report mailed Sep. 26, 2007, in International Patent Application No. PCT/US2006/060315, filed Oct. 27, 2006, 2 pages.

Written Opinion of the International Searching Authority for Int'l Application No. PCT/US2012/071255, mailed Jul. 3, 2014, 6 pages.

* cited by examiner

HOLOGRAPHIC ADAPTIVE SEE-THROUGH PHOROPTER

CROSS-REFERENCE TO RELATED APPLICATIONS

The present application is a continuation of PCT/US12/71255, filed on 21 Dec. 2012, which claims priority to U.S. Provisional Patent Application Ser. No. 61/630,889, filed 21 Dec. 2011, and the present application is a continuation-in-part of U.S. patent application Ser. No. 13/165,231, filed 21 Jun. 2011, which is a continuation-in-part of U.S. patent application Ser. No. 11/426,224, filed on 23 Jun. 2006 (now U.S. Pat. No. 7,993,399), which is a continuation-in-part of U.S. patent application Ser. No. 11/259,781, filed on 27 Oct. 2005 (now abandoned), all of which are incorporated by reference herein in their entirety.

BACKGROUND OF THE INVENTION

A see-through adaptive phoropter provides the ability to automatically measure a patient's refractive prescription while allowing the patient to view targets at both near and far distances. The system automatically measures the patient's refractive error and compensates for it to bring a distant eye chart into focus. Current adaptive phoropter systems use reflective deformable mirrors to compensate for aberrations in the eye. The concept of the Shack Hartmann sensor coupled with adaptive optics originated in the 1990's through research performed at the University of Rochester. These systems were rather large and applied reflective rather than refractive optics. When reflective deformable optics are used, it is difficult to configure the phoropter so that it is compact and mobile. It is therefore desirable to provide phoropters with better characteristics.

SUMMARY OF THE INVENTION

A phoropter having a line of sight for a viewer to see through comprises a lens system in the line of sight, wherein a shape or focal length of at least one lens in the lens system is controllable by means of an electrical signal, electrical field or current. Wavefront sensors of the phoropter detect local tilts of light wavefronts emerging from the eye and generate output signals that are used for controlling the shape or focal length of the at least one lens. Holographic or diffractive elements are used to collect light scattered from an eye of the viewer and image the scattered light to the wavefront sensors. Preferably one or more of the holographic or diffractive elements are away from the line of sight of the viewer.

Refractive error of an eye may be detected by the following process. Light scattered from an eye is passed to a lens system comprising at least one lens in the lens system controllable by means of an electrical signal, field or current. Light scattered from the eye that passed through the lens system is conveyed to wavefront sensors by one or more holographic or diffractive elements. The elements image the scattered light to the wavefront sensors, and cause the sensors to provide output signals containing information on local tilts of light wavefronts emerging from the eye. The output signals are compared to reference signals of an eye model to provide correction signals. A shape or focal length of the at least one lens is adjusted in response to the correction signals to reduce the local tilts of light wavefronts emerging from the eye. Preferably one or more of the holographic or diffractive elements are away from the line of sight of the eye.

All patents, patent applications, articles, books, specifications, standards, other publications, documents and things referenced herein are hereby incorporated herein by this reference in their entirety for all purposes. To the extent of any inconsistency or conflict in the definition or use of a term between any of the incorporated publications, documents or things and the text of the present document, the definition or use of the term in the present document shall prevail.

BRIEF DESCRIPTION OF THE DRAWINGS

Identical components in this application are labeled by the same numerals.

DETAILED DESCRIPTION OF EXEMPLARY EMBODIMENTS

Figure 1:
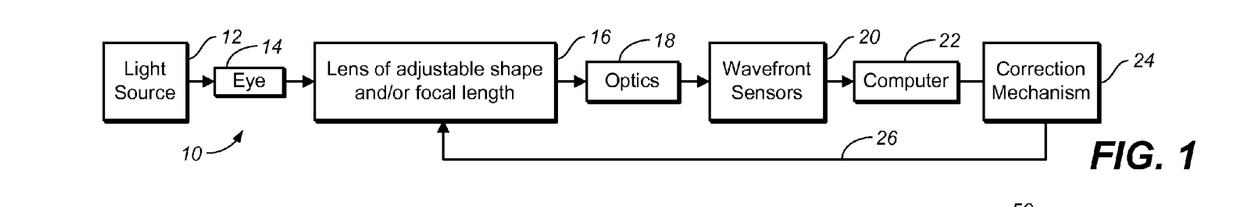
FIG. 1 is a flow chart of a process illustrating an embodiment of the invention.

FIG. 1 is a flow chart of a process 10 illustrating an embodiment of the invention. Light from a light source 12, such as an infrared (IR) or near infrared light source supplies light to an eye 14. The IR light that scatters from the retina of the eye is refracted by the eye and focused by lenses in a lens system 16, where at least one of the lenses has adjustable shape or focal length, or both. One or more lenses in the lens system 16 may be a fluidic lens whose convexity or concaveness can be changed by pumping fluid into or withdrawing fluid from the lens. For a detailed description of fluidic lens construction and operation, please see Marks et al., "Astigmatism and Defocus Wavefront Correction Via Zernike Modes Produced with Fluidic Lenses," Applied Optics, Vol. 48, No. 19, Jul. 1, 2009, pp. 3580-3587. Types of lenses whose shape and/or focal length are adjustable other than fluidic lenses may also be used for lens system 16, such as those described in U.S. Pat. No. 7,993,399, where the shape and/or focal length of lenses are adjustable in response to electrical fields or currents. Still other types of lenses whose shape and/or focal length are adjustable may be used. Please see Valley et al., "Tunable-Focus Flat Liquid-Crystal Diffractive Lens," Optics Letters, Vol. 35, No. 3, Feb. 1, 2010, pp. 336-338 for details of such lenses.

The light scattered by eye 14 and focused by lens system 16 is imaged by optics 18 onto wavefront sensors 20. Preferably, optics 18 includes holographic or diffractive optical elements so that the optical path can be much reduced for constructing a compact phoropter. The holographic or diffractive optical elements are flat glass plates with diffractive structures encoded on their surfaces. These structures can selectively act like a lens and/or beamsplitter leading to splitting of the light and imaging. In the implementations described below, Shack-Hartmann wavefront sensors are used for wavefront sensors 20, although other types of wavefront sensors may be used instead. For examples and details of other types of wavefront sensors, please see Molebny, et al., "Principles of Ray Tracing Aberrometry," Journal of Refractive Surgery, Volume 16, September/October 2000, pp. S572-S575; and Liu et al., "Z-View™ Diffractive Wavefront Sensor—Principle and Applications," Proc. Of SPIE, Vol. 6018, 2005, pp. 601809-1 to 601809-9.

The outputs of the wavefront sensors are sent to a computer 22 which compares the outputs to reference signals obtained from a model eye with perfect vision, and provides correction signals for correcting the sphero-cylindrical error of the eye 14. The correction signals are applied to a correction mechanism 24, which causes the shape and/or focal length of the at least one lens in the lens system 16 to be adjusted to null out the local tilts of the wavefront of the light scattered by the eye in a feedback loop 26. The correction signals then indicate the sphero-cylindrical error of the eye for optical prescriptions of the eye.

Figure 2:
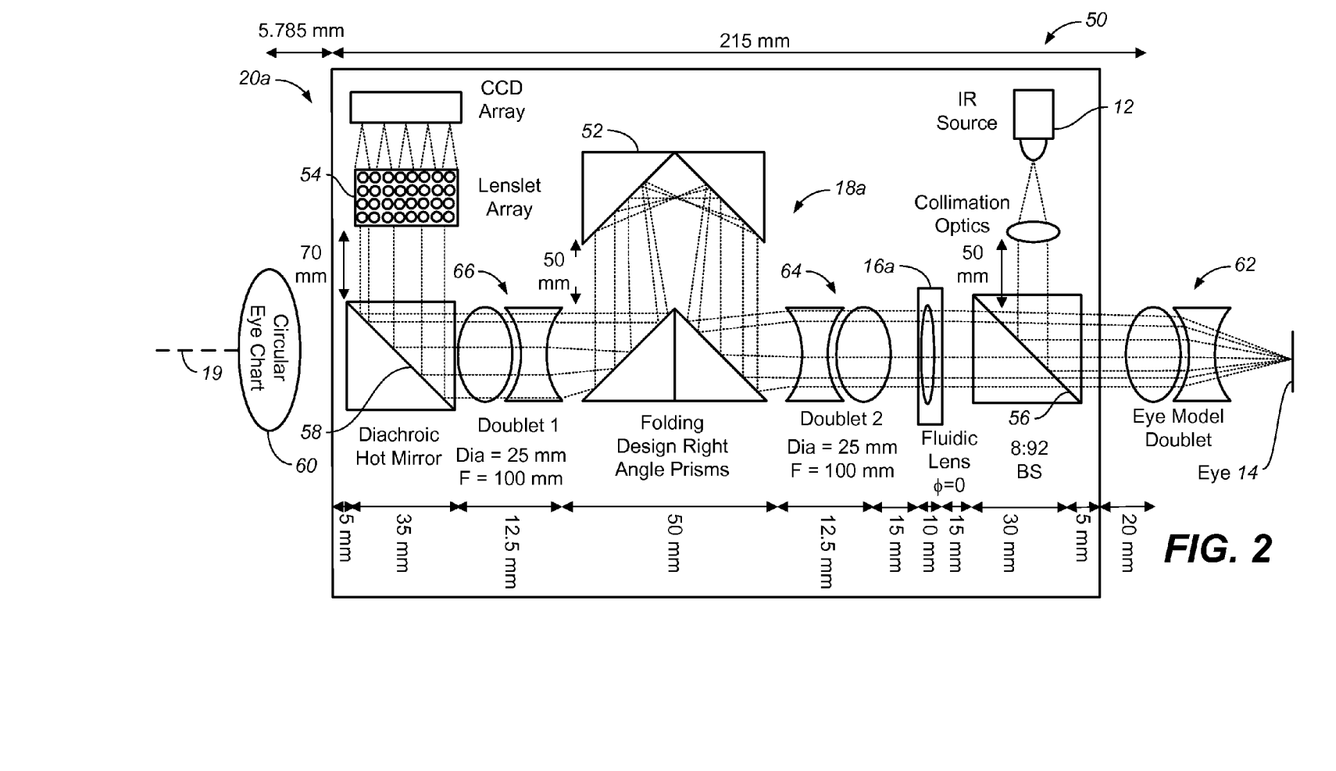
FIG. 2 is a schematic diagram illustrating a first implementation of the embodiment of the invention in FIG. 1, using a holographic telescope in the line of sight.

FIG. 2 is a schematic diagram illustrating a first implementation 50 of the embodiment of the invention in FIG. 1, using a relay holographic telescope 18a in the line of sight 19 which also includes folding mirrors 52. The relay telescope is used to image the eye pupil 14 onto a wavefront measuring device such as an autorefractor or a wavefront sensor. In this implementation, we use a Shack-Hartmann wavefront sensor 20a. This system uses the relay system to image the wavefront emerging from the patient's eye 14 onto a lenslet array 54 of the sensor 20a after reflection from a dichroic mirror 58. The pattern formed by the lenslet array is then analyzed to recover the shape of the wavefront. The lenslet array 54 samples the incident wavefront and provides the wavefront shape information as feedback to the fluidic lens stack 16a as illustrated in FIG. 1. The fluidic lenses are adjusted to null the wavefront error of the eye 14 as best possible. In the current configuration, the sphero-cylindrical error of the eye 14 is corrected. Adding additional fluidic lens modules that correct higher order aberrations would further improve the visual performance of the eye 14.

Similarly, if a measurement of another wavefront plane is necessary, i.e. the spectacle plane, then the spectacle plane would be imaged to the lenslet array 54. The second purpose of the relay telescope is to preserve the shape of the wavefront. If the wavefront exiting the eye 14 is a plane wave, then the wavefront hitting the lenslet array is a plane wave. If the wavefront exiting the eye is a converging spherical wave, then the wavefront hitting the lenslet array is a converging spherical wave. At the far end of the relay telescope is a beamsplitter 56. The beamsplitter 56 directs infrared light from IR source 12 towards the Shack-Hartmann wavefront sensor. The beamsplitter also passes visible light, allowing for the subject to view external targets such as an eye chart 60. The system works as follows: (1) Infrared light is shone into the eye 14 and scatters from the retina, and (2) The scattered light exits the eye 14 as an emerging wavefront that is relayed through the fluidic lens module to the Shack-Hartmann sensor. The sensor reconstructs the wavefront and extracts the sphero-cylindrical refractive error and higher aberrations. This information is used to drive pumps as the correction mechanism 24 to adjust the volume of the fluidic lenses 16a in an attempt to null out the wavefront error. Feedback 26 of the wavefront from the eye/fluidic lens combination is then used to monitor the fluid volume and keep the net refractive error at a minimum. The outcome from the sphero-cylinder portion of the wavefront measurement is the individual's prescription. The eye 14 also sees an eye chart 60 through dichroic mirror 58. Phoropter 10 also includes doublets 62, 64 and 66. Where the shapes and/or focal lengths of lenses are adjustable in response to electrical fields or currents, correction mechanism 24 may include a power source providing such electrical fields or currents in the feedback loop 26.

Figure 3:
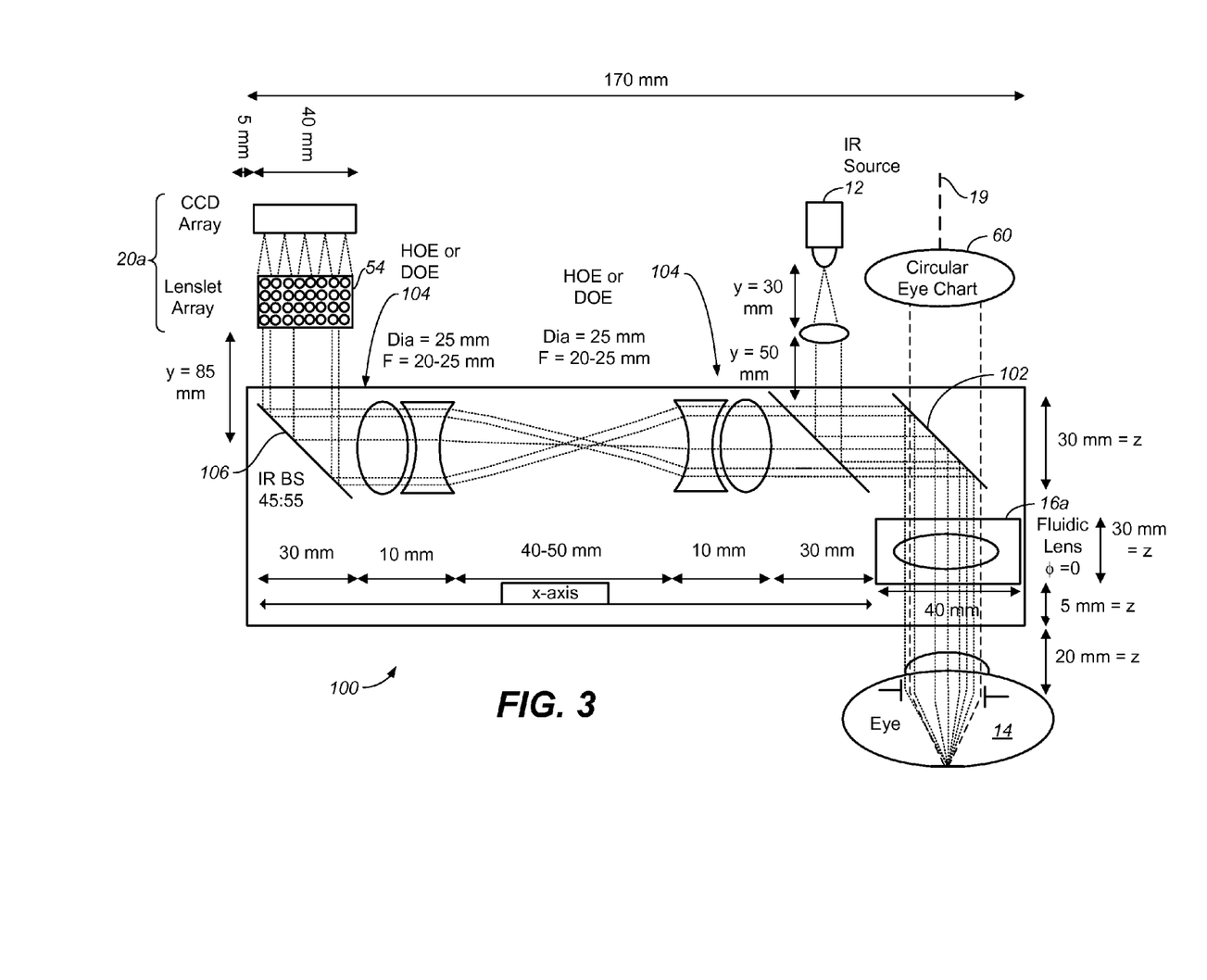
FIG. 3 is a schematic diagram illustrating a second implementation of the embodiment of the invention in FIG. 1, using a holographic telescope away from the line of sight.

FIG. 3 is a schematic diagram illustrating a second implementation 100 of the embodiment of the invention in FIG. 1, using a holographic telescope away from the line of sight 19. With FIG. 3, the eye 14 only observes through a beamsplitter 102 and fluidic lenses 16a. This enables for a wide field of view for both eyes. The holographic or diffractive telescopic system 104 is now off axis enabling us to limit the optics to observe through. There are two advantages of using holographic optical lenses for imaging: 1) Compactness, and 2) Alignment. These optics are flat, allowing for one to slide the lenses in and out without misaligning the system. We were also able to eliminate the folding mirror system 52 in FIG. 2, reducing the complexity of the system. At the same time we are able to compact the system.

The fluidic lens 16a is coupled to beamsplitter 102. The beamsplitter connects the fluidic lens stack to an off axis holographic relay telescope and Shack-Hartman Sensor. The users' field of view is drastically enhanced with only the stack of fluidic lenses and beamsplitter on axis in the user's line of sight 19. The beamsplitter also passes visible light, allowing for the subject to view external targets such as an eye chart 60. The additional modality of the beamsplitter is to direct infrared light from source 12 toward the eye and reflect light back through the off-axis holographic telescopic system to the final module: a Shack-Hartmann wavefront sensor 20a. The holographic telescope 104 applies volume holograms operating in the Bragg Regime to drastically reduce the system size. The holographic optical elements achieve greater than 90% diffraction efficiency with less than a 1% background noise. Our holographic optical elements operate in the infrared and are built at mutually offset angles to produce direct geometry optical lens replication. The system works as follows to measure refractive error of the eye 14: (1) Infrared light from source 12 is reflected by beam splitter 102 and shone into the eye and scatters from the retina, and (2) The scattered light exits the eye as an emerging wavefront that is relayed through the fluidic lens and IR beam splitter 106 to the Shack-Hartmann sensor 20*a*. The sensor reconstructs the wavefront and extracts the sphero-cylindrical refractive error.

This prescription is then applied in feedback loop 26 of FIG. 1 to adjust the volume of the fluidic lenses in an attempt to null out the refractive error. Feedback of the wavefront from the eye/fluidic lens combination is then used to monitor the fluid volume and keep the net refractive error at a minimum. The users' field of view is drastically enhanced with the HOE in the line of sight 19 of the user as we can produce large substrates. This allows for the system field of view to be limited by the fluidic phoropter and no longer by the auto-phoropter design. We have built a binocular system to concurrently measure refractive error of both eyes. The prototype adjusts for the patient's intraocular separation and fits in approximately a 60 mm long by 240 mm wide area.

Our prototype will have the capability of measuring a spherical refractive error from −25 to 25 D, and also the capability of measuring cylindrical refractive error from −8 to 8 D, as well as higher order aberrations. The Shack Hartmann sensor is capable of measuring spherical refractive error from −25 D to 40 D. Even in cases of extreme myopia or hyperopia, a limited number of spots are needed to drive the fluidic lens power in an appropriate direction, forcing the Shack-Hartmann pattern into a more useable range. The range of the prototype may be increased to beyond the limits of the Shack-Hartmann sensor through further experimentation with system controls. Fluidic lenses coupled with a Shack-Hartmann sensor applied in an eye examination have the potential of creating an automated means of measuring and nulling a subject's refractive error. A reliable binocular device is thus produced that allows for quick and inexpensive objective measurement of a subject's refractive error.

The telescopic system and the lenslet array of the Shack-Hartmann wavefront sensor are composed of standard optical lenses. There are many advantages to shifting from traditional optics to holographic optical elements (HOE's). HOE's are lighter, quickly repeatable, and cost much less than traditional optics. Adding HOE technology to our existing fluidic auto-phoropter design will also assist in miniaturizing our optical design as single HOE elements can become transparent in certain wavelengths, act as a lens in other wavelengths, and also act as beamsplitters.

The HOE's can be designed to be transparent in the visible wavelengths, allowing for the eye 14 of the subject to view external targets such as an eye chart 60 with ease. The HOE's additional desired capabilities are to direct infrared light toward the eye and to act as a lens at the 785 nm wavelength. When the HOE acts as a lens, it is at a designed wavelength and that wavelength range is towards an off axis location where a second HOE is placed for the telescopic system. The exiting light of the off-axis holographic telescopic system reaches the final module: a Shack-Hartmann wavefront sensor 20*a*. The desired wavelength of the holographic optical elements operates in the infrared and produce direct geometry optical lens replication.

Our desired wavelength was at 785 nm for reading and writing. There were no HOE's available that operating at this wavelength. For testing purposes, the standard wavelength of 633 nm was applied into our fluidic auto-phoropter. However, the design with this wavelength will also function essentially the same way when IR at 785 nm is used. Thus, if the system operates at 633 nm for reading and writing then it should operate at 785 nm once the technology for this wavelength becomes available.

Gabor zone plates, Fresnel lenses and volume hologram lenses were options for the creation of HOE optical lenses. Fresnel lenses work efficiently with profiled grooves when refraction and diffraction angles of these grooves are matched. However groove profiling drops lens resolution and there is a degradation of image quality. The best viable option was the use of volume holograms in the design of our holographic lenses under designed conditions. In the past couple of years there has been a progression of polymer based volume holograms. Our volume holograms apply the Bayer photopolymer, which is a new holographic recording material developed in the past half decade, in the creation of our volume holograms. For details on the Bayer photopolymer, please see Jurbergs et al., "New Recording Materials for the Holographic Industry," Proc. of SPIE, Vol. 7322, 2009, pp. 72330K-1 to 72330K-10.

There are several advantages in applying Bayer photopolymer based volume holograms as our lenses. From a design stand point, the Bayer material does not require chemical or thermal treatment, which makes them cheap and easily replicable. From an optical standpoint, under certain conditions these HOE's exhibit high optical qualities. The main restrictions of the HOE's for our fluidic holographic auto-phoropter is that the HOEs geometry can be designed as a lens for only a particular wavelength because (1) focal length of the holographic lenses is roughly proportional to the operating wavelength and (2) HOEs work efficiently in only off-axis geometries known as Bragg's angle and this diffraction angle is also wavelength dependent.

In our approach we are using volume holograms as our holographic lenses operating in the Bragg regime, which requires off axis geometry when operable. Standard HOE's are designed in the visible wavelength where our HOE's was designed at 633 nm for testing purposes. The HOE's appear on 2.3 mm thick glass substrates with a rectangular shape and have a 2 inch diameter size. HOEs recorded in such a regime can achieve more than 90% diffraction efficiency, less than 1% background noise, a transparency in wavelength ranges from 350 nm to 1500 nm, and high angular selectivity.

The high angular sensitivity of the holographic lens allows for almost no diffraction outside of the controlled angular range. This allows for the rest of the range between 350 nm to 1500 nm to be transparent. Thus when the HOE is designed at 785 nm, the HOE will act as a clear window in the visible where the viewer looks through while at the same time acts as a lens at the wavelength of 785 nm off axis. As one of these HOE's functions as a lens off axis, and as shown in the implementation 150 of FIG. 4, we have now replaced the need for a beamsplitter as the HOE lens 152 in the line of sight 19 functions as a lens at our operating wavelength 633 nm, but simultaneously acts as a beamsplitter with a clear window in the rest of the visible spectrum. At our operating wavelength, we have high diffraction efficiency of over 90% with negligible amounts of background noise. Instead of losing approximately half the operating light every interaction with the beamsplitters, we now lose less than 10% of the light from each of the holographic lenses.

Figure 4:
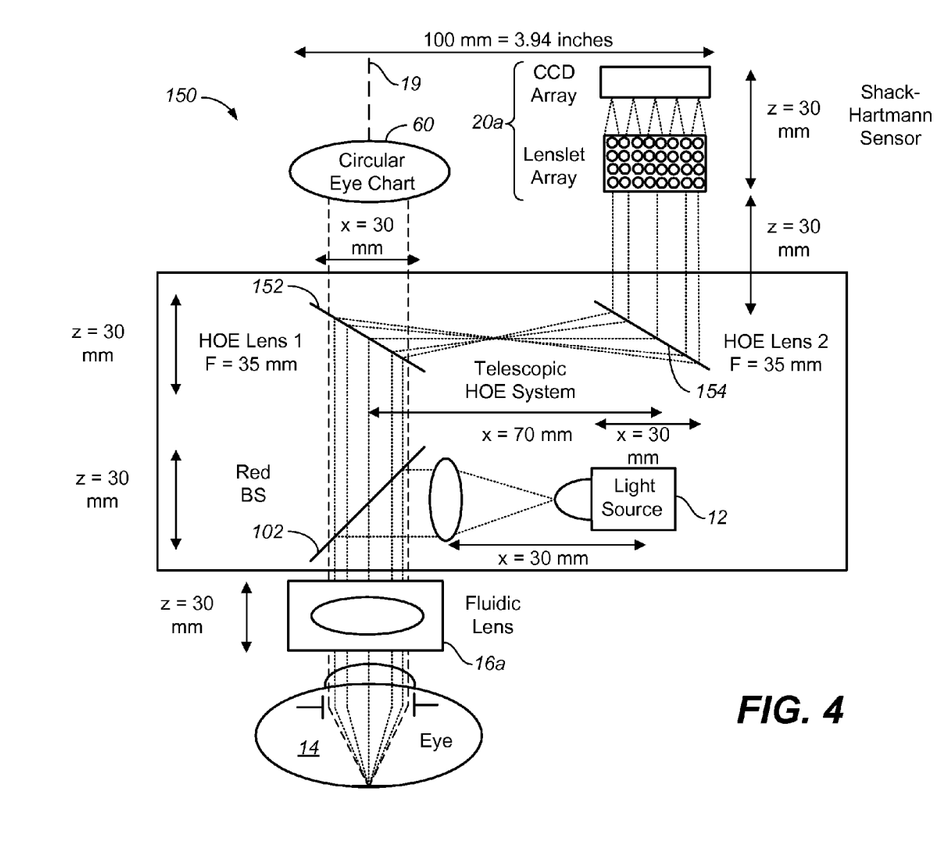
FIG. 4 is a schematic diagram illustrating a third implementation of the embodiment of the invention in FIG. 1, using a holographic telescope where one of the holographic lenses of the telescope is away from the line of sight.

FIG. 4 is a schematic diagram illustrating a third implementation of the embodiment of the invention in FIG. 1, using a holographic telescope where one lens 154 of the holographic lenses of the telescope is away from the line of sight 19. Two positive powered HOE lenses 152, 154 are used. The combination of the two HOE lenses at a 2F separation produced a Keplerian holographic telescope with an afocal design. The operating wavelength for the HOE prototype was at a HeNe wavelength of 633 nm. The system was drastically compressed and efficiency improved by removing the beamsplitters in the optical setup. The length in front of the user is still 3.5" in the z-axis for the line of sight 19. The width of the optical system was compressed to 100 mm or roughly 4". The Shack-Hartmann wavefront sensor in this design is described with a position vertically above the second HOE lens in the telescopic system.

Modeling Fluidic Holographic Auto-Phoropter Prototype One

We modeled the holographic auto-phoropter in ZEMAX prior to building the system as shown in the above described embodiments and implementations. The holographic auto-phoropter was modeled so that the two holographic elements were set in a position relative to each other to produce a telescope. After the HOE's were set to produce a holographic telescopic system we began adding components of the holographic auto-phoropter. The light source enters from off axis onto a beamsplitter and half the light reflects toward the eye model. The fluidic phoropter was set at zero power as again we were testing to verify if there was a power variation due to the shifting of the mirror position in the eye model and what range is achievable.

Figure 5:
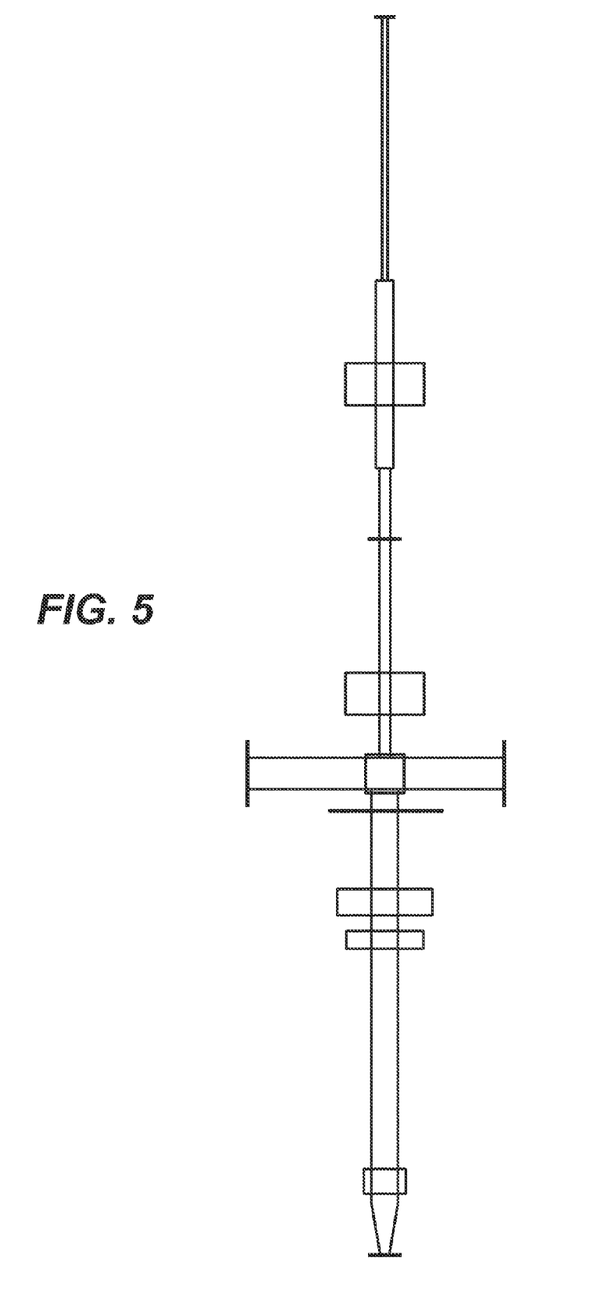
FIG. 5 shows the holographic telescope in alignment with the model eye. This optical path is a representation that the testing light follows through the telescope.
Figure 6:
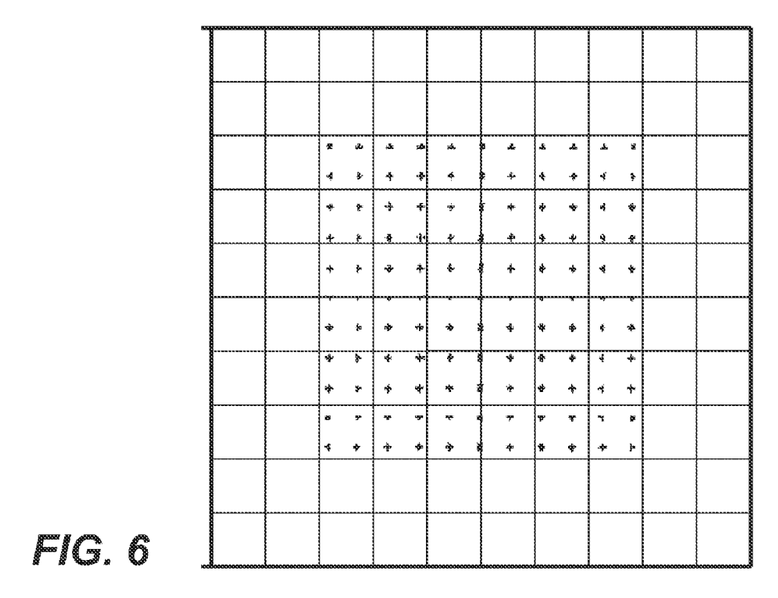
FIG. 6 is a pattern of spots representing output signals from the Shack-Hartmann wavefront sensors in the third implementation of FIG. 4, representing local slopes of a wavefront of the light scattered by a model eye with perfect vision, when the lens system of such implementations applies zero power.

FIG. 5 shows the holographic telescope in alignment with the model eye. This optical path is a representation that the testing light follows through the system and not the path that the user observes through the system. FIG. 6 is a pattern of spots representing output signals from the Shack-Hartmann wavefront sensors in the third implementation of FIG. 4, representing local slopes of a wavefront of the light scattered by a model eye with perfect vision, when the lens system of such implementations applies zero power.

Figure 7A:
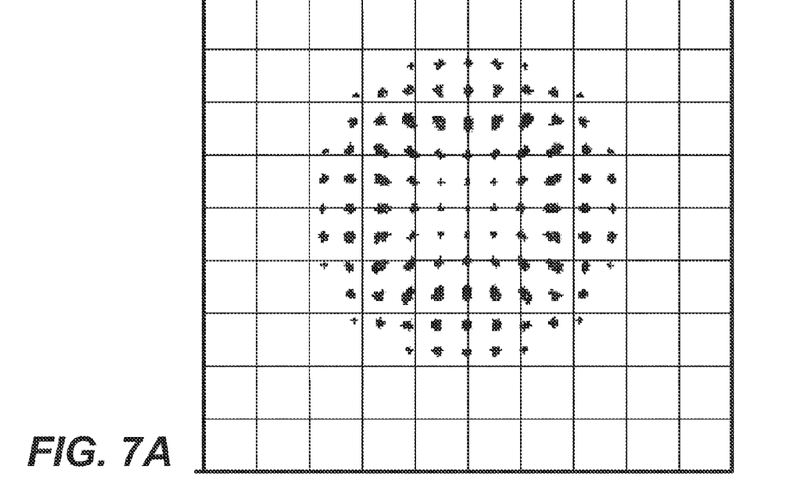
FIGS. 7A, 7B are patterns of spots representing output signals from the Shack-Hartmann wavefront sensors in the third implementation of FIG. 4, where the patterns show the point separation and shifts relative to mirror position in the model eye. As the points focused closer to the detector plane, the resolution between points diminished.
Figure 7B:
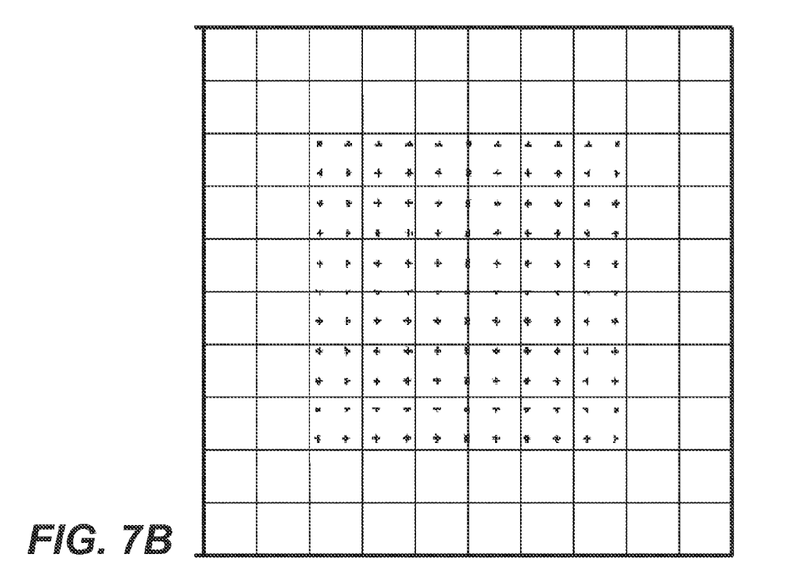

Once our model was fully aligned we tested power variation of the model eye caused by shifting the mirror position. The ZEMAX model identified the physical range in which our holographic auto-phoropter functions. The lower limit, as seen in FIG. 7A, 7B, was observed as the lenslet points began focusing on a single point location. The dynamic range that was observed in the physical model was down to about −16 D of power. With the specified optical separations that we modeled in ZEMAX, we were able to model powers that ranged between −15 D to +15 D. FIGS. 7A, 7B are patterns of spots representing output signals from the Shack-Hartmann wavefront sensors in the third implementation of FIG. 4, where the patterns show the point separation and shifts relative to mirror position in the model eye. As the points focused closer to the detector plane, the resolution between points diminished.

In the implementation of FIG. 4, the alignment of the optical system is no longer constructed around the beamsplitters like those of FIGS. 2 and 3 but rather centered around the two HOE lenses. The alignment of the two HOE lenses relative to each other is achieved by taking advantage of two lasers, both operating at the HeNe 633 nm wavelength. Each HOE is aligned individually so that the maximum intensity reaches the focal location of that HOE lens. The HOE's are aligned relative to each other so that the focal location of the two HOE lenses is at the exact same location. The direction of the optical axis for both HOE lenses is preferably exact. Once the HOE's are aligned with the two lasers entering the system from both sides, the telescopic HOE system is ready for use.

The lasers are then removed and the rest of the system is aligned. One of the HeNe lasers is placed off axis and lighter enters the system through beamsplitter 102. Half the light reflects toward the fluidic phoropter and the eye model. We have removed the fluidic phoropter as to test the accuracy of the auto-phoropter system with the eye model. The Shack-Hartmann wavefront sensor was placed at the proper position off axis to HOE lens 2 in order to focus light at the center of the sensor plane.

Promising results were achieved through the testing of the HOE auto-phoropter. It was found that in fact a slope was measurable as we adjusted the defocus power at the model eye location. The linear change in power was measured with shifts of the mirror position at the eye model location, verifying that our holographic fluidic auto-phoropter can in fact measure a shift in power and can compensate for that power. The HOE telescope in some fashion has diminished the slope variation as measured by the wavefront sensor.

The field of view of the holographic design of FIG. 4 increased relative to the other auto-phoropter designs. The size of the substrate that the HOE was embedded in was a 2' or 50.8 mm glass plate. The HOE was set at a 90° angle, giving the lateral width of 36 mm's perpendicular to the optical axis. The furthest distance of the HOE is 115 mm along the optical axis, giving a field of view of 17.3° and hence no longer the limiting object in the line of sight. Again, we calculate the field of view with zero power of the fluidic phoropter. The limiting factor of the optical system now becomes the first beamsplitter that brings the system field of view to 11.8°. We calculate the maximum field passing through the fluidic lens was 14° relative to the 25 mm eye relief distance between the eye and the flat of the fluidic phoropter. In order to maximize the field of view we eliminate the second beamsplitter in FIG. 4 and bring the HOE to a closer distance of the fluidic phoropter. This will cause the fluidic phoropter to become the limitations on the field of view and not the auto-phoropter design.

Figure 8:
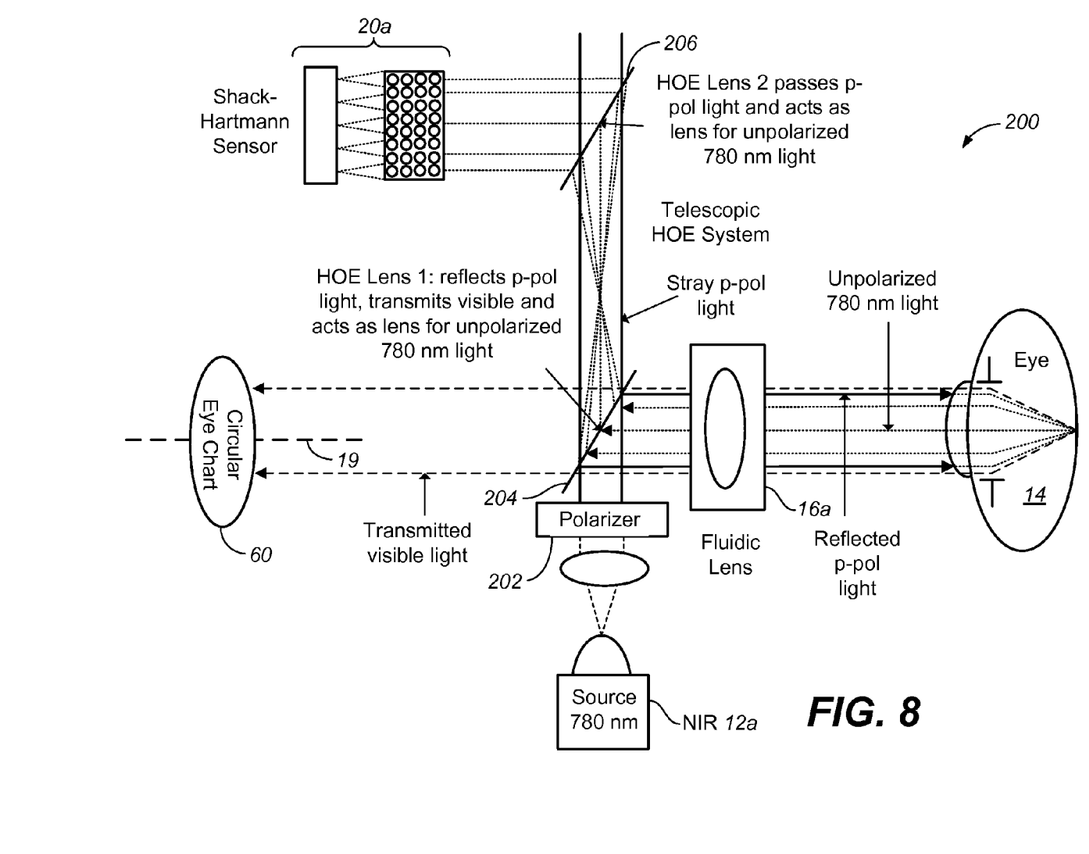
FIG. 8 is a schematic diagram illustrating a fourth implementation of the embodiment of the invention in FIG. 1, using polarized light in a holographic telescope where one of the holographic lenses of the telescope is in the line of sight to replace a beam splitter.

It is possible to redesign the holographic system so that all beamsplitters are eliminated as shown in the design 200 of FIG. 8. FIG. 8 is a schematic diagram illustrating a fourth implementation of the embodiment of the invention in FIG. 1, using polarized light in a holographic telescope where one of the holographic lenses of the telescope is in the line of sight to replace a beam splitter.

This second holographic design 200 takes advantage of polarization in order to eliminate the last remaining beamsplitter 152 of FIG. 4. The near IR (NIR) source 12a will be polarized in the p direction by placing a polarizer 202 in front of the source. The first HOE element 204 will have one or more embedded layers (not shown) that function as a mirror for p-pol light at 785 nm, causing the p-pol light at 785 nm to reflect or diffract. As an aside, there may be stray p-pol light near 785 nm passing through the first HOE to the second HOE 206. The second HOE is designed so that p-pol light at 785 nm passes the light through the element in order to eliminate the stray light from the system. Regressing, the 785 nm light that reflects off of the first HOE is in the line of sight 19 of the user. This p-pol light propagates through the fluidic lens to the human eye or the model eye with the scattering screen. The majority of the light exiting the retina upon reflection is no longer polarized. The unpolarized NIR light propagates back to HOE Lens 204. HOE Lens 204 is now a lens to the unpolarized light and becomes part of our telescopic system. HOE Lens 206 is placed at a proper distance from HOE Lens 204 to produce our telescopic system. The light exiting the second HOE 206 then propagates to the Shack-Hartman wavefront sensor 20a, thus eliminating all beamsplitters from the optical system. The comparison of the output signals from the Shack-Hartman wavefront sensor 20a to the reference pattern obtained from the model can be done in a manner similar to that for other implementations described above.

We can expand further with our polarization controlled HOE design 200 of FIG. 8 in eliminating the shortfall of lacking 4F imaging. The reason we broke the 4f design was to miniaturize the system. If we were to produce a 4F imaging system with the polarization controlled design we would need space for two elements between HOE lens 204 and the eye for the fluidic phoropter and eye relief. The minimum distance of these two optical elements is approximately 60 mm when we include tolerance. Therefore, the shortest focal length for 4f imaging with HOE's is with the two HOE lenses exhibiting focal lengths of 60 mm and polarization control. The length between the two HOE's would be 120 mm or approximately 4.7 inches. This size would be small enough to fit on a helmet sized fluidic auto-phoropter if desired. If we rotate the optical axis instead so we maximize Bragg efficiency the height in the vertical direction will be less than 4.7 inches, hence making it more suitable for a helmet sized holographic fluidic auto-phoropter design. Therefore, our holographic designs is advanced by a table top setup with two HOE lenses designed with 60 mm focal lengths at a wavelength of 785 nm that have polarization control as described in FIG. 9.

Figure 9:
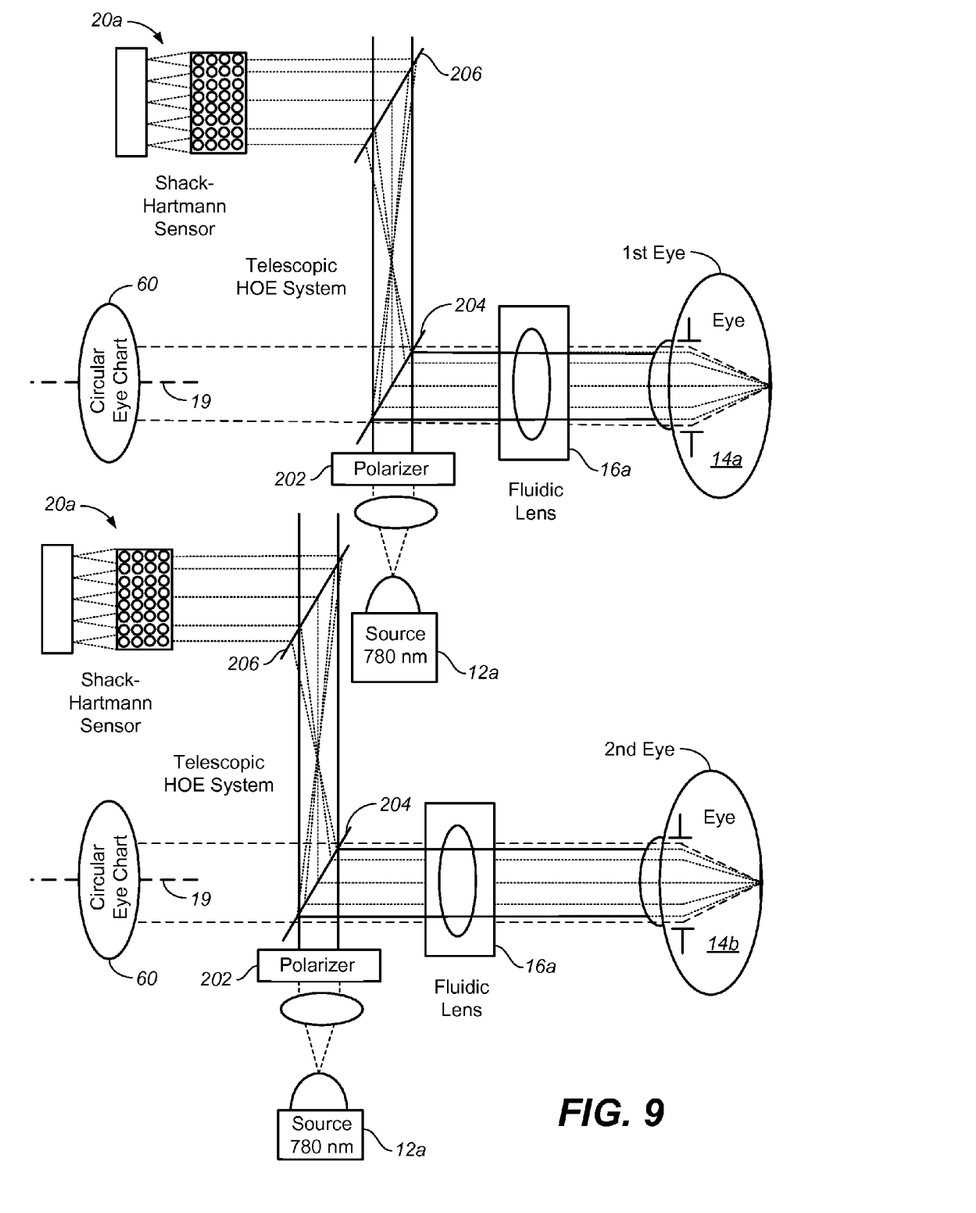
FIG. 9 is a schematic diagram of a binocular phoropter comprising two phoropters located adjacent to each other, for simultaneous viewing by both eyes of a viewer illustrating another embodiment of the invention.
Figure 10A:
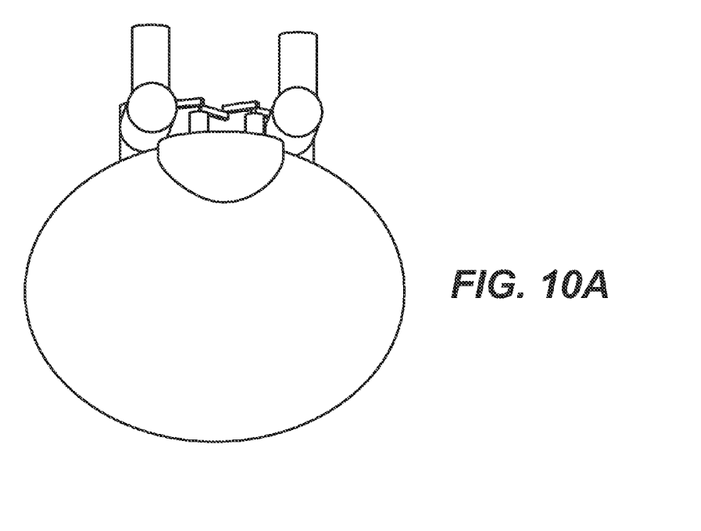
FIGS. 10A, 10B and 10C are views of a helmet from different perspectives, where the helmet houses and holds the binocular phoropter of FIG. 9
Figure 10B:
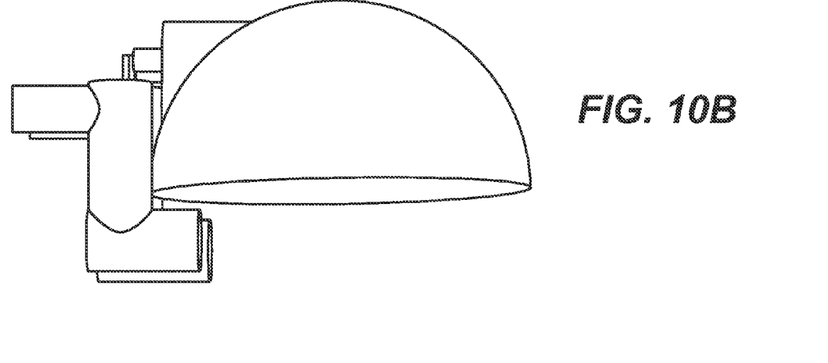
Figure 10C:
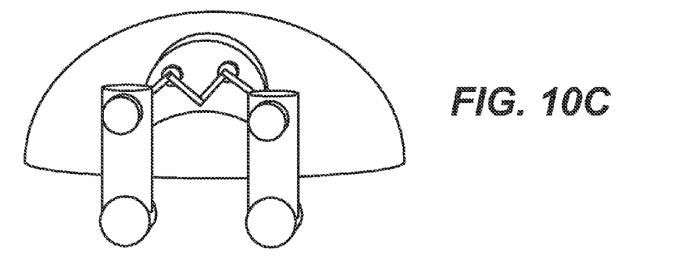

There are many disadvantaged regions in the world that do not have access to phoropters and eye care. It would be highly advantageous for a phoropter system to become mobile. FIG. 9 is a schematic diagram of a binocular phoropter comprising two phoropters located adjacent to each other, for simultaneous viewing by both eyes 14a, 14b of a viewer illustrating another embodiment of the invention. FIGS. 10A, 10B and 10C are views of a helmet from different perspectives, where the helmet houses and holds the binocular phoropter of FIG. 9.

As is seen in FIGS. 9 and 10A-10C, the size of our 4F advanced holographic fluidic auto-phoropter can fit within a helmet. This helmet can hold two of these optical systems next to each other. The next step after testing and verifying that this system functionally measures and corrects for prescriptions is to set the system into a helmet and make it mobile. The helmet display was modeled in SolidWorks to identify the coupling of the two holographic auto-phoropters into a single system. The actuators (not shown) for the fluid pump controls would be inside the periphery of the casing. The inter-pupilary distance is taken into account by adjusting the separation on the helmet with a knob (not shown) between the two monocular setups.

While the invention has been described above by reference to various embodiments, it will be understood that changes and modifications may be made without departing from the scope of the invention, which is to be defined only by the appended claims and their equivalents.

What is claimed is:

1. A phoropter having a line of sight for a viewer to see through, comprising:
   a lens system in the line of sight, wherein a shape or focal length of at least one lens in the lens system is controllable by means of an electrical signal, field or current;
   wavefront sensors configured to detect local tilts of light wavefronts emerging from the eye and generate output signals for controlling the shape or focal length of said at least one lens; and
   one or more holographic or diffractive elements away from the line of sight configured to collect light scattered from an eye of the viewer and image the scattered light to said wavefront sensors, and wherein the phoropter is configured with no mirror element in the line of sight.

2. The phoropter of claim 1, further comprising an infrared or near infrared light source configured to illuminate the eye, wherein infrared or near infrared light scattered by the eye and imaged onto the wavefront sensors by the holographic elements causes the wavefront sensors to generate said output signals.

3. The phoropter of claim 2, wherein the holographic or diffractive elements are substantially transparent to and do not image visible light onto the wavefront sensors.

4. The phoropter of claim 2, further comprising a beam splitter in the line of sight to direct the infrared or near infrared light and pass visible light to the eye in the line of sight and to pass the scattered infrared or near infrared light to the holographic or diffractive elements.

5. The phoropter of claim 2, wherein said infrared or near infrared light source is configured to supply polarized light to the eye, and one of the holographic or diffractive elements is located in the line of sight, said one of the holographic elements having a layer that diffracts the polarized infrared or near infrared light from the source.

6. The phoropter of claim 1, said phoropter capable of measuring a spherical refractive error from −25 to 25 D.

7. The phoropter of claim 1, said phoropter capable of measuring cylindrical refractive error from −8 to 8 D, said phoropter further capable of measuring higher order aberrations.

8. The phoropter of claim 1, wherein the at least one lens in the lens system changes shape in response to a flow of fluid into or out of the at least one lens, said phoropter further comprising a pump configured to fluid to and withdraw fluid from the at least one lens to change its shape.

9. The phoropter of claim 8, further comprising a computer configured to compare the output signals to signals generated for a model eye and provide said electrical signal to control the pump.

10. A binocular phoropter having a line of sight for a viewer to see through, comprising two phoropters located adjacent to each other, for simultaneous viewing by both eyes of a viewer, wherein each of the two phoropters comprises:
    a lens system in the line of sight, wherein a shape or focal length of at least one lens in the lens system is controllable by means of an electrical signal, field or current;
    wavefront sensors configured to detect local tilts of light wavefronts and generate output signals for controlling the shape or focal length of said at least one lens; and
    one or more holographic or diffractive elements away from the line of sight configured to collect light scattered from an eye of the viewer and image the scattered light to said wavefront sensors, and wherein the phoropter is configured with no mirror element in the line of sight.

11. The binocular phoropter of claim 10, wherein a distance between the two phoropters is adjustable.

12. The binocular phoropter of claim 10, further comprising a helmet that houses said two phoropters.

13. A phoropter having a line of sight for a viewer to see through, comprising:
    a lens system in the line of sight, wherein a shape or focal length of at least one lens in the lens system is controllable by means of an electrical signal, field or current;

wavefront sensors configured to detect local tilts of light wavefronts and generate output signals for controlling the shape or focal length of said at least one lens; and holographic or diffractive elements away from the line of sight configured to collect light scattered from an eye of the viewer and image the scattered light to said wavefront sensors, and wherein the phoropter is configured with no mirror element in the line of sight.

14. A method for detecting refractive error of an eye, comprising:

passing light scattered from the eye through a lens system comprising at least one lens in the lens system controllable by means of an electrical signal, field or current;

conveying light scattered from the eye that passed through the lens system to wavefront sensors by one or more holographic or diffractive elements away from line of sight of the eye, wherein said conveying is in the absence of a mirror element in the line of sight, said elements imaging the scattered light to said wavefront sensors, and causing said sensors to provide output signals containing information on local tilts of light wavefronts emerging from the eye;

comparing said output signals to reference signals of an eye model to provide correction signals; and adjusting a shape or focal length of the at least one lens in response to the correction signals to reduce the local tilts of light wavefronts emerging from the eye.

* * * * *